United States Patent [19]

Isogai

[11] Patent Number: 5,625,428
[45] Date of Patent: Apr. 29, 1997

[54] OPHTHALMIC APPARATUS WITH ALIGNMENT INDICATING SYSTEM

[75] Inventor: Naoki Isogai, Nishio, Japan

[73] Assignee: Nidek Co., Ltd., Japan

[21] Appl. No.: 219,895

[22] Filed: Mar. 30, 1994

[30] Foreign Application Priority Data

Mar. 31, 1993 [JP] Japan ................... 5-098941

[51] Int. Cl.$^6$ ................. A61B 3/14; A61B 3/10
[52] U.S. Cl. ................. 351/208; 351/211; 351/221
[58] Field of Search ................. 351/211, 212, 351/247, 246, 205, 221, 218; 128/648, 645

[56]  References Cited

U.S. PATENT DOCUMENTS 4,705,045  11/1987  Nishimura ................. 128/648

FOREIGN PATENT DOCUMENTS 61-85920  5/1986  Japan.

Primary Examiner—William L. Sikes
Assistant Examiner—Hung Xuan Dang
Attorney, Agent, or Firm—Rossi & Associates

[57] ABSTRACT

An ophthalmic apparatus for measuring and observing an eye of an examinee comprising an observing optical system through which an examiner observes the examinee's eye, and a displaying device for providing indication marks to the cornea of the eye, the indication marks showing necessary information for the operator, wherein images of the indication marks reflected by the cornea are observed as superimposed on the examinee's eye.

10 Claims, 3 Drawing Sheets

OPHTHALMIC APPARATUS WITH ALIGNMENT INDICATING SYSTEM

BACKGROUND OF THE INVENTION

1. Field of the Invention

The present invention relates to an ophthalmic apparatus for measuring and observing an eye and, more particularly, to an ophthalmic apparatus provided with a system to indicate alignment information and others to an operator.

2. Description of Related Art

Ophthalmic apparatuses for measuring and observing generally have optical systems for observing an examinee's eye, because those apparatuses require the accurate alignment between the apparatus and the examinee's eye. For the observing optical system, there are some kinds of an optical system for photographing the examinee's eye with a CCD camera and the like and then projecting the image of the eye on a TV monitor, and another optical system for directly observing the examinee's eye through an observing lens.

The former system commonly displays the alignment information and examined data with the image of the eye in the same field of view on a TV monitor, by introducing displaying luminous flux to the observing optical system or by utilizing a character displaying circuit and a graphic displaying circuit and the like.

The latter direct observing system utilizes introducing luminous flux for displaying the information into an observing optical system and, alternatively, displaying the information at out of observation visual field of an examiner so that the examiner observes the examinee's eye and a display portion alternately.

However, the former system should be provided with CCD cameras and TV monitors and others and therefore causes the increased cost of apparatus and large-sized apparatus. The system is not suitable at all for hand-held type apparatus consequently.

An apparatus with the latter system, wherein a display unit is disposed at out of the observation visual field of the examiner, has a troublesome problem that the the examiner must turn his eye on the examinee's eye and the display alternately. The system for introducing the luminous flux from the display unit into the observation visual field must provide the optical path for the displaying luminous flux and dispose a light synthesizing member. Accordingly, the apparatus with the system, increasing in size, is not always suitable for hand-held type apparatus.

SUMMARY OF THE INVENTION

The present invention has been made in view of the above circumstances and has an object to overcome the above problems and to provide an ophthalmic apparatus having a system by which the examiner can obtain the information with his eye turning on the examinee's eye, and usable for hand-held type apparatus.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus for measuring and observing an eye of an examinee of this invention comprises observing optical system through which an examiner observes the examinee's eye, and displaying means for providing indication marks to the cornea of the examinee's eye, the indication marks showing necessary information for the operator, wherein images of the indication marks reflected by the cornea are observed as superimposed on the examinee's eye.

In another aspect of the present invention, an ophthalmic apparatus for measuring the shape of the cornea of an examinee's eye comprises an observing optical system for observing the examinee's eye, an index projecting optical system for projecting an index onto the examinee's eye to measure the shape of the cornea, a detecting optical system for detecting the index projected by the index projecting optical system, an alignment detecting optical system for projecting indexes for alignment including working distance onto the examinee's eye and for detecting images of the indexes reflected by the cornea, displaying means for displaying alignment condition through the observing optical system, and measured data displaying means for displaying measured data obtained by the detecting optical system, wherein the each component is comprised in an apparatus body of a hand-held type apparatus, and displaying luminous flux from the measured data displaying means is introduced to the cornea of the examinee's eye, so that the examiner observes the measured data through the observing optical system.

According to the present invention, with a very simple construction, the examiner can obtain useful information to operate the apparatus without turning his eye from the examinee's eye.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
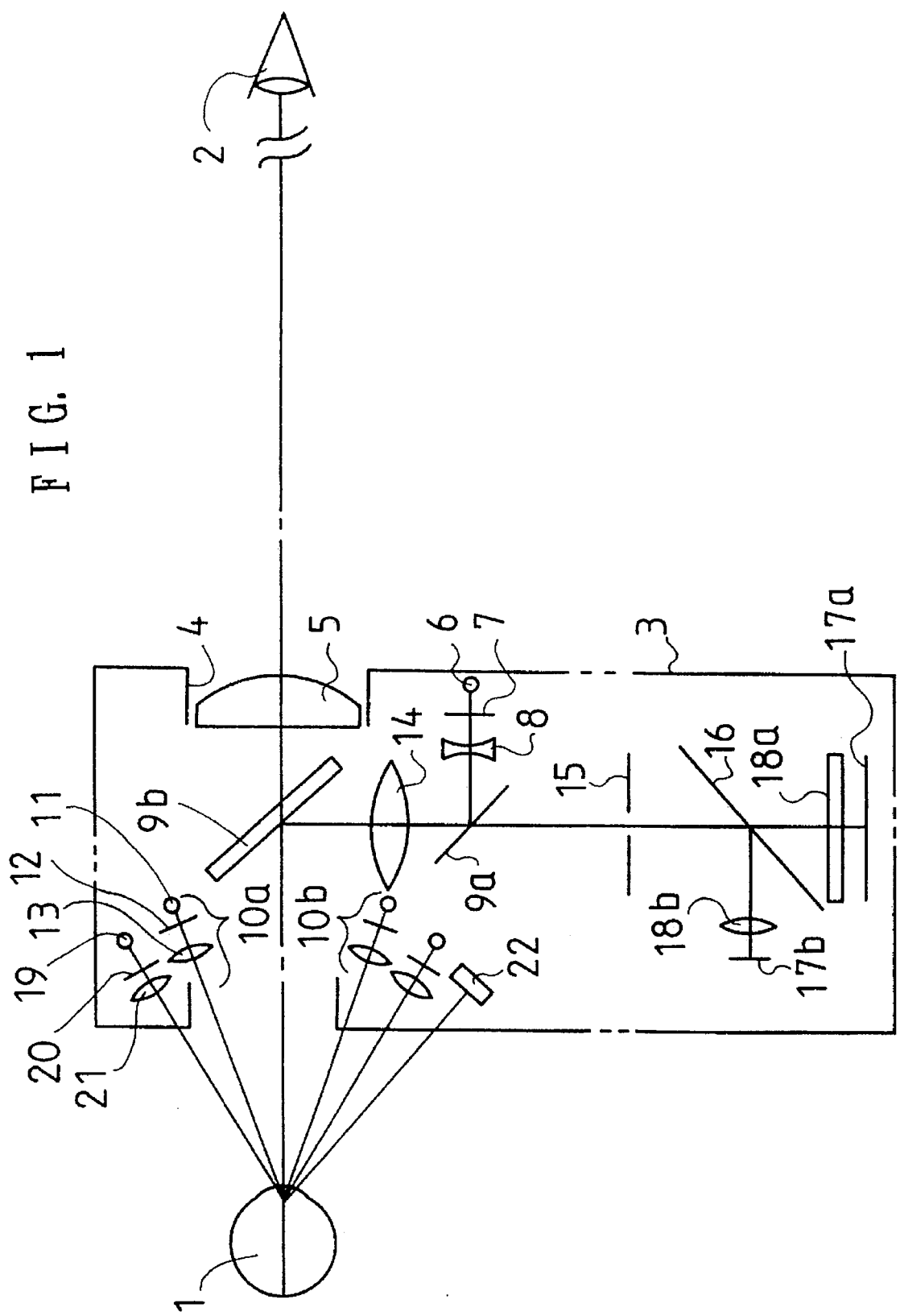
FIG. 1 is a diagram to show an optical arrangement of an optical system of an ophthalmic apparatus according to the present invention.

FIG. 1 shows a side view of an optical system of an ophthalmic apparatus in the embodiment.

Numeral 1 indicates an eye of an examinee and numeral 2 indicates an eye of an examiner respectively. In FIG. 1, the apparatus body 3, which is a cornea shape measurement apparatus of hand-held type in the present embodiment, is provided with a through hole 4 through which the examiner can observe the examinee's eye 1, and an objective lens 5 fitted in the through hole 4. The examiner's eye 2 therefore observes the examinee's eye 1 through the objective lens 5 for magnifying the examinee's eye in monocular vision. The present embodiment utilizes an apparatus for monocular observation, but can also use an apparatus for binocular observation.

The apparatus body 3 further includes an illumination light source 6 for fixation target, a fixation target plate 7 provided with a spot aperture, a concave lens 8 for projecting an image of the fixation target on the fundus of the examinee's eye 1 in cooperation with a focusing lens mentioned below, and a dichroic mirror 9a for reflecting an optical axis of light of fixation target coaxially to an optical axis of detecting optical system, a beam splitter 9b for reflecting a light of fixation target coaxially to a light of observing optical system, and index projecting optical systems 10a–10d for measuring the shape of a cornea of the examinee's eye 1.

Figure 2:
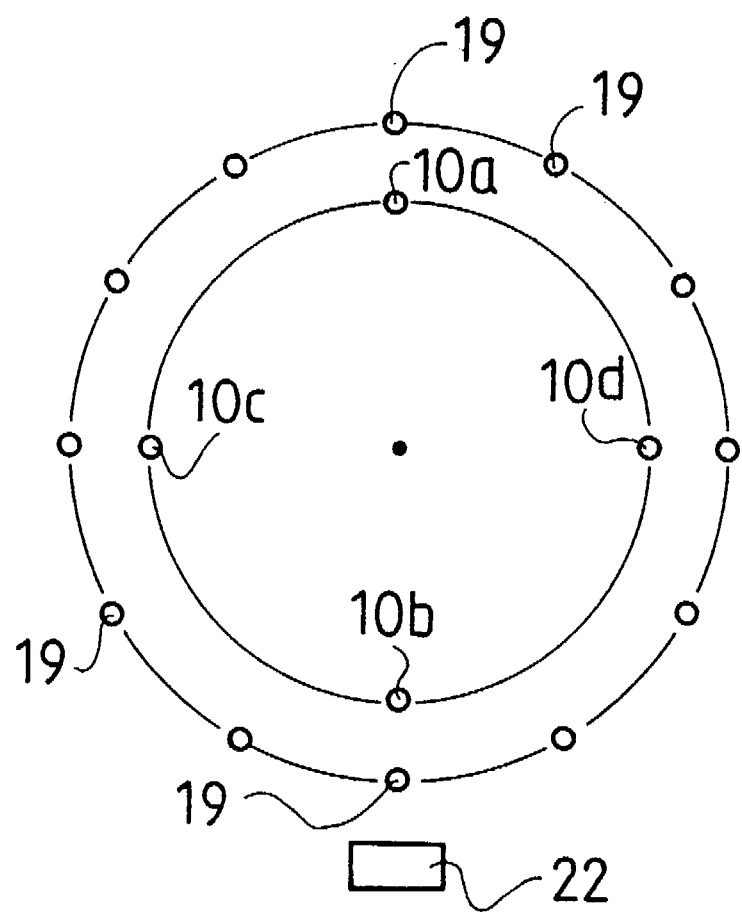
FIG. 2 is a schematic diagram to show an arrangement of index projecting optical systems and LEDs.

The index projecting optical systems 10a–10d are arranged, as shown in FIG. 2, at 90-degrees angle apart from each other in the same circle centering the optical axis of the observing optical system, each of which is constituted of a LED 11 for emitting light of near infrared area, a spot diaphragm 12 and a collimator lens 13. When detecting working distance (alignment condition), the collimator lens 13 of the index projecting optical system 10a is disposed out of the optical path. Technical context thereof has been disclosed in Japanese Patent Application No. 4(1992)-224896 corresponding to U.S. Pat. No. 5,463,430.

In the apparatus body 3, also provided are a focusing lens 14, a telecentric diaphragm 15 arranged at a focus point of the focusing lens 14, a beam splitter 16 for dividing light into two light beams, one-dimensional image sensors 17a and 17b each of which is arranged on each optical path of two light beams so as to cross their detecting directions with each other, and cylindrical lenses 18a and 18b. The cylindrical lenses 18a and 18b are disposed between the telecentric diaphragm 15 and each of the one-dimensional image sensors 17a and 17b respectively so that each axis of the cylindrical lenses 18a and 18b coincides with each detecting directions of the image sensors 17a and 17b.

LEDs 19 are disposed at regular intervals in a circle (twelve LEDs in the present embodiment, as shown in FIG. 2), each of which is provided with a spot diaphragm 20 and a collimator lens 21. Spot light from the LEDs 19 are reflected by the cornea and the cornea reflecting images of the spot light arranged in a circle can be utilized as a substitution for mire-ring. The LED 19 is also used for an indicator to indicate alignment condition of the apparatus, when the alignment condition is indicated by four LEDs 19 disposed at up-and-down and right-and-left positions in the circle.

Numeral 22 shows a display unit for displaying measured data including errors, for which liquid crystal display and dot matrix type display and others are usable. The display unit 22 displays the data in reversed picture, so that the data image is provided for the examiner as normal image when the reversed image is projected on and reflected by the cornea. A display unit for displaying normal pictures is also usable in the embodiment if the normal picture is reversed by a mirror to be projected on the cornea. The display unit 22 can display measured data and an indication showing a right or left eye, which is input by the examiner, so that the examiner can look the information including the measured data as superimposed on the examinee's eye.

Operation of the apparatus described above will be explained as below.

The examinee looks fixedly at a fixation target image from the fixation target light source 6 and the plate 7, and the examiner observes the examinee's eye 1 through the objective lens 5 to magnifying the eye. Observing the examinee's eye as above, the examiner conducts alignment operation in accordance with the following procedure simultaneously.

Alignment in vertical and horizontal directions is detected based on positions of index images provided of the index projecting optical systems 10c and 10d reflected by the cornea of the eye 1, which are arranged symmetrically to the optical axis of measuring light, more specifically, based on direction or distance of the coordinates of a middle point between two index images in comparison with the coordinates of a middle point which ought to be positioned in proper alignment.

Figure 3:
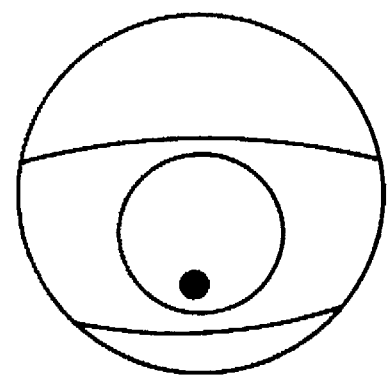
FIG. 3 is a schematic diagram to explain alignment operation.

The light of index images reflected by the cornea are reflected by the beam splitter 9b toward the focusing lens 14 and then focused by the focusing lens 14 on the one-dimensional image sensors 17a and 17b along each detecting direction. The one-dimensional image sensors 17a and 17b detect two-dimensional positions of the index images reflected by the cornea. Microcomputer (not shown) processes coordinates of a middle point between the index images and compares it with coordinates of a middle point which ought to be positioned in proper alignment. As a result, if the measuring optical axis is positioned upward to the examinee's eye 1, LED 19 disposed at a lower position is turned on (or blinked on and off) to show the examiner a direction to move the apparatus, as shown in FIG. 3. The examiner moves the apparatus in the moving direction accordingly. As soon as alignment in vertical and horizontal directions is completed, LEDs 19 disposed in a moving direction, i.e., at up-and-down and right-and-left positions respectively are turned on.

To adjust working distance of the apparatus, the following operation is conducted.

The collimator lens 13 of the index projecting optical system 10a is first removed out of the optical path to detect the working distance. And then, regarding index images reflected by the cornea, one of which is provided by the index projecting optical system 10a and another by the index projecting optical system 10b, their images height are compared. This utilizes the characteristics that, if the working distance is changed, height of the index image formed by a light source at infinity is settled, but that of the index image formed by a light source at finity is changeable, if the working distance is changed. The detailed explanation thereof is described in U.S. Pat. No. 5,463,430 proposed by the present applicant.

The image height of index images formed by the finite light source and the infinite light source respectively are compared based on the result detected at the one-dimensional image sensors 17a and 17b, and thereby suitability of the working distance is judged. LEDs 19 are slowly blinked on and off if the apparatus is closer to the examiner compared with the proper working distance, and rapidly blinked on and off if the apparatus is too close to the examinee's eye 1.

Completing the alignment as above, measuring the shape of a cornea of the examinee's eye 1 is succeedingly conducted. The shape of a cornea can be calculated if three index images are detected as described in Japanese Laid-Open Patent No. 61(1986)-85920. It is therefore possible to measure the shape of the cornea as the collimator lens 13 of the index projecting optical system 10a is stayed out of the optical path. In the present embodiment, however, to obtain more accurate data, the collimator lens 13 of the optical system 10a is moved into the optical path by a motor when a signal is generated to indicate completion of alignment, so that the shape of a cornea is measured based on four coordinates of index images provided by the four index projecting optical systems 10a–10d.

The data for the shape of the cornea processed at the microcomputer is displayed in the display unit 22 through a displaying circuit, and the displaying luminous flux of the display unit 22 is turned toward the cornea of the examinee's eye 1. The examiner can observe the data image reflected by the cornea as superimposed on the examinee's eye.

The present invention may be embodied in other specific forms without departing from the spirit or essential characteristics thereof. For instance, the above embodiment utilizes blinking situation of LED 19 to indicate the suitability of the working distance, and besides, a LED emitting two colors; red and green can further be utilized, so that the suitability of the working distance can be indicated with three colors; red, green and orange.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus having a measurement optical system for measuring an eye of an examines, comprising:

an observing optical system for observing an anterior portion of the examinee's eye;

an alignment index projecting optical system for projecting an index onto the examinee's eye to align the examinee's eye and the measurement optical system;

an alignment detecting optical system having a photoelectric conversion element for detecting the index projected by the alignment index projecting optical system;

judging means for judging an alignment condition based on the detected result by the alignment detecting optical system; and displaying means for displaying luminous flux indicative of the judged result of the judging means, whereby the displaying luminous flux is emitted toward the cornea of the examinee's eye so that an examiner is informed of the judged result by observing the luminous flux introduced into the observing optical system after being reflected on the cornea.

2. An ophthalmic apparatus according to claim 1, wherein the measurement optical system comprises:

a measurement index projecting optical system; and a measurement detecting optical system for detecting the measurement index, wherein the alignment detecting system is shared with the measurement optical system.

3. An ophthalmic apparatus according to claim 1, wherein each component is provided in an apparatus body of a hand-held type apparatus.

4. An ophthalmic apparatus for measuring the shape of the cornea of an examinee's eye, comprising:

an observing optical system for observing the examinee's eye;

an index projecting optical system for projecting an index onto the examinee's eye to measure the shape of the cornea;

a detecting optical system for detecting the index projected by the index projecting optical system;

an alignment detecting optical system for projecting indexes for alignment including working distance onto the examinee's eye and for detecting images of the indexes reflected by the cornea;

displaying means for displaying alignment condition through said observing optical system; and measured data displaying means for displaying measured data obtained by said detecting optical system, wherein displaying luminous flux from the measured data displaying means is introduced to the cornea of the examinee's eye, so that the examiner observes the measured data through the observing optical system.

5. An ophthalmic apparatus for measuring the shape of the cornea of an examinee's eye, comprising:

an observing optical system for observing the examinee's eye;

an index projecting optical system for projecting an index onto the examinee's eye to measure the shape of the cornea;

a detecting optical system for detecting the index projected by the index projecting optical system;

an alignment detecting optical system for projecting indexes for alignment including working distance onto the examinee's eye and for detecting images of the indexes reflected by the cornea;

displaying means for displaying alignment condition through said observing optical system; and measured data displaying means for displaying measured data obtained by said detecting optical system, wherein said each component is comprised in an apparatus body of a hand-held type apparatus, and displaying luminous flux from the measured data displaying means is introduced to the cornea of the examinee's eye, so that the examiner observes the measured data through the observing optical system.

6. An ophthalmic apparatus according to claim 5, wherein said observing optical system is provided with means for magnifying the examinee's eye to be observed.

7. An ophthalmic apparatus according to claim 5, wherein said index projecting optical system includes removably a collimator lens which changes index light from finite light to infinite light and the reverse, and the apparatus further comprises working distance judging means for judging suitability of the working distance by comparing both height of index images, one of which is projected by the infinite light when the collimator lens is disposed in an optical path of the index projecting optical system, another of which is projected by the finite light when the collimator lens is disposed out of the optical path.

8. An ophthalmic apparatus according to claim 5, wherein said alignment condition displaying means is constituted of light emitting element group arranged in plural circles on vertical planes to the optical axis of the observing optical system, and one or plural light emitting elements of which disposed in the adjusting direction are turned on if said alignment detecting optical system judges that the alignment condition is unsuitable.

9. An ophthalmic apparatus according to claim 8, wherein light sources of mire-ring projecting optical system for projecting mire-ring images into the eyeball of the examinee's eye are substituted for the light emitting element group of said alignment condition displaying means.

10. An ophthalmic apparatus according to claim 5, further comprising fixation target projecting optical system for projecting a fixation target to the examinee's eye.

* * * * *